United States Patent [19]
Eberhard et al.

[11] Patent Number: 5,611,026
[45] Date of Patent: Mar. 11, 1997

[54] COMBINING A PRIORI DATA WITH PARTIAL SCAN DATA TO PROJECT THREE DIMENSIONAL IMAGING OF ARBITRARY OBJECTS WITH COMPUTERIZED TOMOGRAPHY

[75] Inventors: Jeffrey W. Eberhard; Kristina H. V. Hedengren, both of Schenectady, N.Y.

[73] Assignee: General Electric Company, Schenectady, N.Y.

[21] Appl. No.: 500,387

[22] Filed: Jul. 10, 1995

Related U.S. Application Data

[63] Continuation of Ser. No. 994,240, Dec. 21, 1992, abandoned.

[51] Int. Cl.⁶ .................................................. A61B 6/03
[52] U.S. Cl. .................................................. 395/119
[58] Field of Search ........................ 395/119, 121; 345/137; 364/413.14–413.23; 378/4, 8, 95; 382/131–132

[56] References Cited

U.S. PATENT DOCUMENTS

| | | | |
|---|---|---|---|
| 4,506,327 | 3/1985 | Tam | 364/413.19 |
| 4,751,644 | 6/1988 | Koka et al. | 364/413.21 |
| 4,752,691 | 6/1988 | Hawman | 250/363.1 |
| 4,803,639 | 2/1989 | Steele et al. | 364/507 |
| 4,878,169 | 10/1989 | Toner et al. | 364/413.19 |
| 4,888,693 | 12/1989 | Tam | 364/413.16 |
| 4,920,491 | 4/1990 | Eberhard et al. | 364/413.19 |
| 4,942,596 | 7/1990 | Eberhard et al. | 378/109 |
| 4,969,110 | 11/1990 | Little et al. | 364/413.21 X |
| 4,977,505 | 12/1990 | Pelizzari et al. | 364/413.19 |
| 5,023,895 | 6/1991 | McCroskey et al. | 378/4 |
| 5,029,221 | 7/1991 | Takiguchi et al. | 382/132 |
| 5,032,990 | 7/1991 | Eberhard et al. | 364/413.15 |
| 5,034,969 | 7/1991 | Ozaki | 378/4 X |
| 5,043,890 | 8/1991 | King | 364/413.21 |
| 5,053,958 | 10/1991 | Tam | 364/413.13 |
| 5,056,020 | 10/1991 | Feldman et al. | 364/413.19 |
| 5,068,882 | 11/1991 | Eberhard | 378/4 |
| 5,073,910 | 12/1991 | Eberhard et al. | 378/4 |
| 5,073,911 | 12/1991 | Ozaki et al. | 364/413.21 X |
| 5,218,534 | 6/1993 | Trousset et al. | 364/413.17 |
| 5,241,471 | 8/1993 | Trousset et al. | 364/413.19 |
| 5,260,873 | 11/1993 | Hishinuma | 364/413.19 X |
| 5,270,926 | 12/1993 | Tam | 364/413.19 |
| 5,325,296 | 6/1994 | Eberhard | 364/413.15 |
| 5,365,560 | 11/1994 | Tam | 378/8 |
| 5,375,156 | 12/1994 | Kuo-Petravic et al. | 364/413.15 X |
| 5,376,795 | 12/1994 | Hasegawa et al. | 364/413.24 X |
| 5,383,119 | 1/1995 | Tam | 364/413.19 |
| 5,485,492 | 1/1996 | Pelc | 378/5 |

OTHER PUBLICATIONS

"Quantitative Cone–Beam Reconstruction", Hui Hu et al., SPIE vol. 1092 Medical Imaging III: Image Processing (1989), pp. 492–501.

"The Dynamic Spatial Reconstructor", Robb et al., Journal of Medical Systems, vol. 4, No. 2, 1980, pp. 253–288.

"Practical Cone–Beam Algorithm", Feldkamp et al., J. Opt. Soc. Am. A/vol. 1, No. 6, Jun. 1984, pp. 612–619.

(List continued on next page.)

*Primary Examiner*—Mark K. Zimmerman
*Assistant Examiner*—Anton W. Fetting
*Attorney, Agent, or Firm*—David C. Goldman; Marvin Snyder

[57] ABSTRACT

The present invention discloses a method and a system for supplementing and completing 3D CT data generated from an incomplete scanning path. If a detector is large enough to scan the object, additional data is acquired from adjacent scanning paths and combined directly with the original projection data set in order to form an exact and complete data set called the combined data set. If the object to be scanned is larger than the detector, additional data from adjacent scanning paths is acquired and reconstructed into an approximate image of the adjacent region from which appropriate projection data from the region of interest is calculated to form an exact and complete data set. In either case, a priori information about the object may be used to calculate missing projection information.

6 Claims, 10 Drawing Sheets

OTHER PUBLICATIONS

"Convolutional Reconstruction From Cone–Beam Projection Data", G. N. Minerbo, IEEE Transaction on Nuclear Science, vol. NS–26, No. 2, Apr. 1979, pp. 2682–2684.

"An Inversion Formula for Cone–Beam Reconstruction", H. K. Tuy, Siam J. Appl. Math., vol. 43, No. 3, Jun. 1983, pp. 545–552.

"Image Reconstruction from Cone–Beam Projections: Necessary and Sufficient Conditions and Reconstruction Methods", Bruce D. Smith, IEEE Transactions on Medical Imaging, vol. MI–4, No. 1, Mar. 1985, pp. 14–25.

"Iterative Three–Dimensional Reconstruction from Twin–Cone Beam Projections", M. Schlindwein, IEEE Transactions on Nuclear Science, vol. NS–25, No. 5, Oct. 1978, pp. 1135–1143.

"Algebraic Reconstruction Techniques (ART) for Three–Dimensional Electron Microscopy and X–Ray Photography", Gordon et al., J. Theor. Biol. (1970) 29, pp. 471–481.

"Tomographic Reconstruction from Experimentally Obtained Cone–Beam Projections", Webb et al., IEEE Transactions on Medical Imaging, vol. M1–6, No. 1, Mar. 1987, pp. 67–73.

"Cone–Beam Tomography: Recent Advances and a Tutorial Review", Bruce D. Smith, Optical Engineering, May 1990, vol. 29, No. 5, pp. 524–534.

"Analysis of a 3D Imaging System by Reconstruction from X Radiographies in Conical Geometry", Pierre Grangeat, Doctoral Thesis, pp. 1–303.

Patent Application Serial No. 07/992,673, filed Dec. 18, 1992, by J. W. Eberhard.

Patent Application Serial No. 07/992,672, filed Dec. 18, 1992, by J. W. Eberhard et al.

Patent Application Serial No. 07/998,330 filed Dec. 30, 1992, by J. W. Eberhard et al.

COMBINING A PRIORI DATA WITH PARTIAL SCAN DATA TO PROJECT THREE DIMENSIONAL IMAGING OF ARBITRARY OBJECTS WITH COMPUTERIZED TOMOGRAPHY

This application is a Continuation of application Ser. No. 07/994,240 filed 21 Dec. 1992, abandoned.

BACKGROUND OF THE INVENTION

The present invention relates to three dimensional computerized tomography. More specifically, the present invention relates to completing or supplementing incomplete scanning path data from cone beam three dimensional (3D) computerized tomography (CT).

In conventional computerized tomography for both medical and industrial applications, an x-ray fan beam and a linear array detector are used. Two-dimensional (2D) imaging is achieved. While the data set may be complete and image quality is correspondingly high, only a single slice of an object is imaged at a time. When a 3D image is required, a stack of slices approach is employed. Acquiring a 3D data set one 2D slice at a time is inherently slow. Moreover, in medical applications, motion artifacts occur because adjacent slices are not imaged simultaneously. Also, dose utilization is less than optimal because the distance between slices is typically less than the x-ray collimator aperture, resulting in double exposure to many parts of the body. In 2D CT, the scanning path of the source is often simply circular scan about the object. The linear array detector is fixed relative to the source. (Although it is usual to talk about a scan path of a source relative to the object to be imaged, it is to be appreciated that the object may be rotated or otherwise moved to provide relative motion between the object and the source.)

In a system employing true cone beam geometry for 3D imaging, a cone beam x-ray source and a 2D area detector are used. An object is scanned, preferably over a 360° angular range, either by moving the x-ray source in a scanning circle about the object or by rotating the object while the source remains stationary. In either case, the area detector is fixed relative to the source. The relative movement between the source and object which is to be imaged provides scanning in either case. Compared to the conventional 2D stack of slices approach to achieve 3D imaging, the cone beam geometry has the potential to achieve rapid 3D imaging of both medical and industrial objects with improved dose utilization.

The standard scanning path used in cone beam 3D CT imaging is a single circular scan of source and detector about the object. However, the data acquired in a single scanning circle can be shown to be incomplete for 3D CT imaging.

Complete 3D data scanning paths are known, but they are often complex. For example, U.S. Pat. No. 5,073,910 issued Dec. 17, 1991 to the present inventors discloses a complete data scanning path. That patent, which is assigned to the present assignee, is hereby incorporated by reference.

The criteria for data set completeness relative to scanning path in a 3D CT System are described in the paper by Bruce D. Smith entitled "Image Reconstruction from Cone-Beam Projections: Necessary and Sufficient Conditions and Reconstruction Methods", IEEE Transactions on Medical Imaging, Volume MI-4, No. 1, pages 14–25 (March 1985), hereby incorporated by reference.

Depending upon the particular object being viewed and the particular circumstances, it may be unnecessary to obtain a complete data scan under the criteria explained in the Smith article. Moreover, under some circumstances, it may be impossible or difficult to obtain a complete scan. There are occasions when data from an incomplete scan path is obtained under these and other circumstances such as when one initially thinks that the incomplete scan data will be sufficient for a particular purpose.

After obtaining incomplete scan path data relative to a particular object (as used herein, the object may be a workpiece or a medial patient or other thing which is being imaged), one may conclude that more accurate data is required in order to give an image satisfactory under the particular circumstances. For example, the incomplete scan path data may provide a satisfactory image over most of the object, but one may notice a particular portion of the object having an irregularity which must be imaged more accurately. Under such circumstances, one might simply start the imaging process over using a complete data scan path (in spite of the greater complexity of such a scan path) or at least using a scan path which will provide a more accurate image of the portion of the object associated with the irregularity. However, it may be difficult or inconvenient to perform a further scan on the object. For example, the object might be a work piece which had been imaged sufficiently satisfactorily that it was approved for use in a particular design and sent to another location for assembling the workpiece with other components of a machine. However, the engineers or others who are supervising assembly of the design may change the design such that the workpiece must now be checked for defects which would not have been a problem in the original design. In order to retest the particular workpiece under the more stringent criteria, the workpiece may have to be shipped back to the original testing location. This is a rather expensive and time-consuming step. Even under those circumstances where an object, such as a workpiece, is readily available for further scanning, further additional scanning may take some time to accomplish. Additionally, further scanning of the object may be convenient under certain circumstances, but may require one to repeat the original scan path in addition to adding lines or curves to the scan path.

OBJECTS AND SUMMARY OF THE INVENTION

Accordingly, it is a primary object of the present invention to provide an improved 3D CT imaging technique.

A more specific object of the present invention is to provide a technique for supplementing 3D CT data from an incomplete data scanning path.

Yet another object of the present invention is to provide a technique for completing data from a 3D CT incomplete data scanning path.

Yet another object of the present invention is to provide a technique for supplementing incomplete 3D CT image data without necessarily requiring further scanning of the object.

A still further object of the present invention is to provide a technique for 3D CT imaging wherein an initial incomplete data set from an incomplete data scan path can be supplemented or even completed without requiring a repetition of the initial incomplete data scan path.

The above and other objects of the present invention which will become apparent as the description proceeds are realized by a method of three-dimensional computerized tomography imaging of at least a region of interest of an object subject to imaging energy. Imaging energy is applied from a source to the object. The source is moved relative to the object in a incomplete data scan path. An incomplete, initial data set relative to a region of interest is acquired by using an area detector to sense imaging energy. A supplemental data set at least partially representative of image information about the region of interest is obtained. The supplemental data set is combined with the initial data set to provide a combined data set. An image is displayed of at least the region of interest of the object based upon the combined data set.

A first method according to the present invention performs the obtaining step by moving the source relative to the object in a supplemental scan path which, when combined with the incomplete data scan path, constitutes a complete scan path. As used herein, a complete scan path is one which provides complete data as described in the above-mentioned Smith article. The combined data set is a complete data set.

A second method according to the present invention performs the obtaining step by using first portion data from a first portion of the incomplete data scan path, which first portion data corresponds to the approximate image of a first part of the region of interest, using second portion data from a second portion of the incomplete data scan path, which second portion data corresponds to an approximate image of a second part of the region of interest, and using the first and second portion data to calculate the supplemental data set.

The supplemental data set is, according to one aspect of the present invention, data corresponding to a simulated scan path, which, when combined with the incomplete data scan path, would constitute a complete data scan path.

According to another aspect of the present invention the obtaining step is performed by acquiring first adjacent data corresponding at least partly to an approximate image of a first adjacent region adjacent to the region of interest and acquiring second adjacent data corresponding at least partly to an approximate image of a second adjacent region adjacent to the region of interest, the first and second adjacent data being the supplemental data set. The combining step corrects projections at the edges of the region of interest to delete contributions from the first and second adjacent regions.

The system according to the present invention is a three-dimensional computerized tomography system including a source of imaging energy for applying imaging energy to at least a region of interest of an object. A two-dimensional area detector is positioned to receive imaging energy from the source. A scanning means for causing relative motion of the source and the object such that the source moves along incomplete data scan path relative to the object allows the area detector to sense imaging energy to provide an incomplete, initial data set. Means for receiving the initial data set from the area detector are provided. The system further includes a means for causing the obtaining of a supplemental data set at least partly representative of image information about the region of interest. A means for combining the supplemental data set with the initial data set to provide a combined data set is operably connected to a display to display an image of the region of interest based upon the combined data set.

BRIEF DESCRIPTION OF THE DRAWINGS

The above and other features of the present invention will be more readily understood when the following detailed description is considered in conjunction with the accompanying drawings wherein like characters represent like parts throughout the several views and in which.

DETAILED DESCRIPTION OF THE INVENTION

Figure 1:
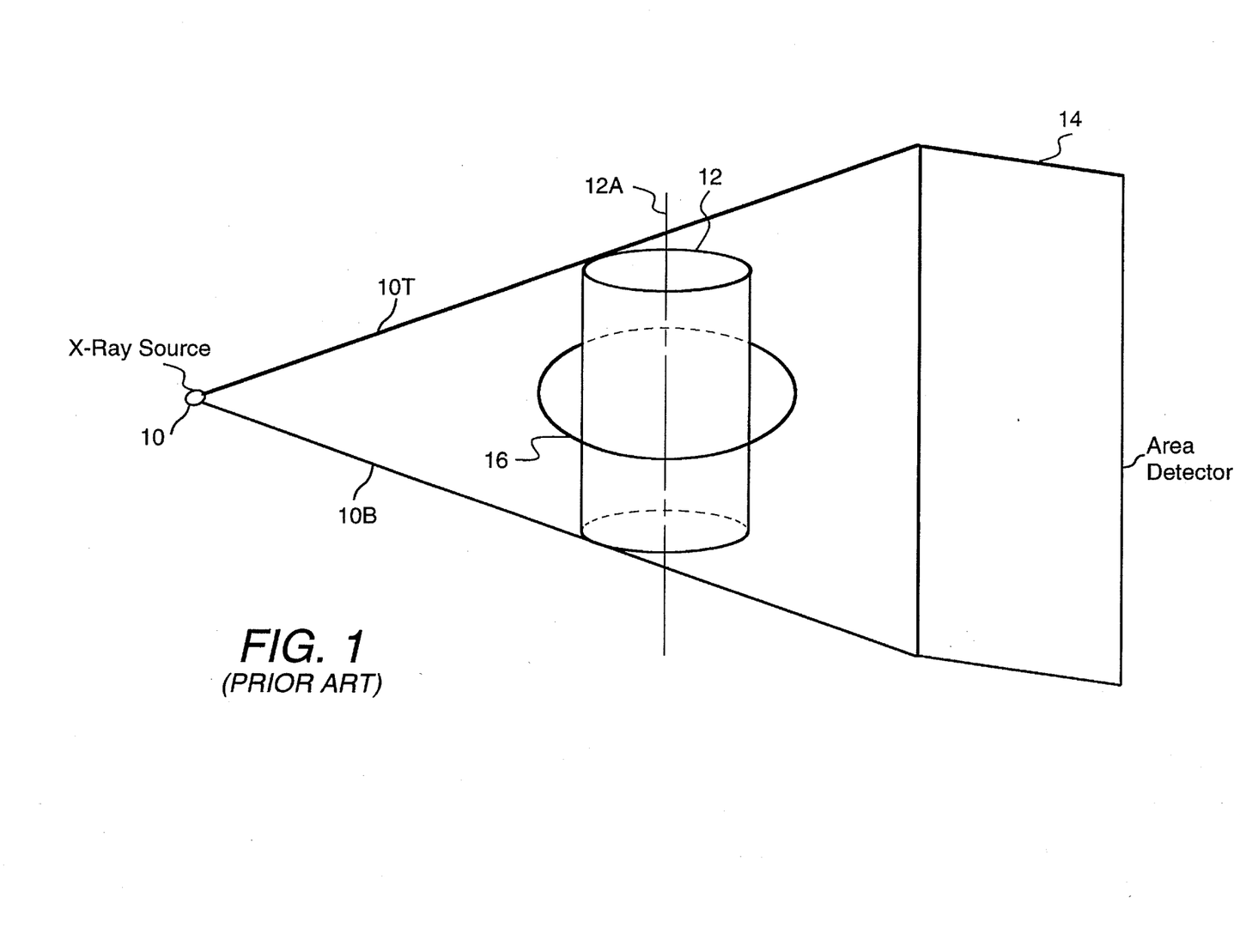
FIG 1 illustrates schematically a prior art incomplete scan path.

Turning now to FIG. 1, an x-ray source 10 is scanned relative to an object 12. A two-dimensional area detector 14 receives the x-ray energy for generating an image of the object 12. In accord with the usual practice, the prior art technique of FIG. 1 would have the source 10 and detector 14 fixed relative to each other and both scanned relative to the object 12. The scanning may be accomplished by maintaining the object 12 stationary while the source 10 and detector 14 are moved, or by maintaining the source 10 and detector 14 stationary while the object 12 is moved. Top and bottom rays 10T and 10B respectively are shown simply to illustrate that the object 12 is disposed completely within the field of view. The scanning is depicted schematically by the circle 16 located at the middle of the object 12, which has been drawn as a cylinder. The scan path 16 as shown may simply illustrate rotation of the cylinder 12 about its central lengthwise axis 12A or may simply indicate a movement of source 10 in a circle centered and perpendicular to the axis 12A. In either case, the relative motion between the source 10 and the object 12 is the same.

Although performing a single circular scan as depicted schematically by circle 16 may be adequate for certain applications, it can be shown (e.g., the previously mentioned Smith article) that such a simple circular scan will provide incomplete data. In order to provide complete data, every plane passing through the object of interest must intersect the source scanning projectory at least once. Since a plane perpendicular to the axis 12A and intersecting the axis near the top of object 12 will not intersect the scanning path, the scanning path depicted schematically by 16 is incomplete. The completeness criterion is not met.

Figure 2:
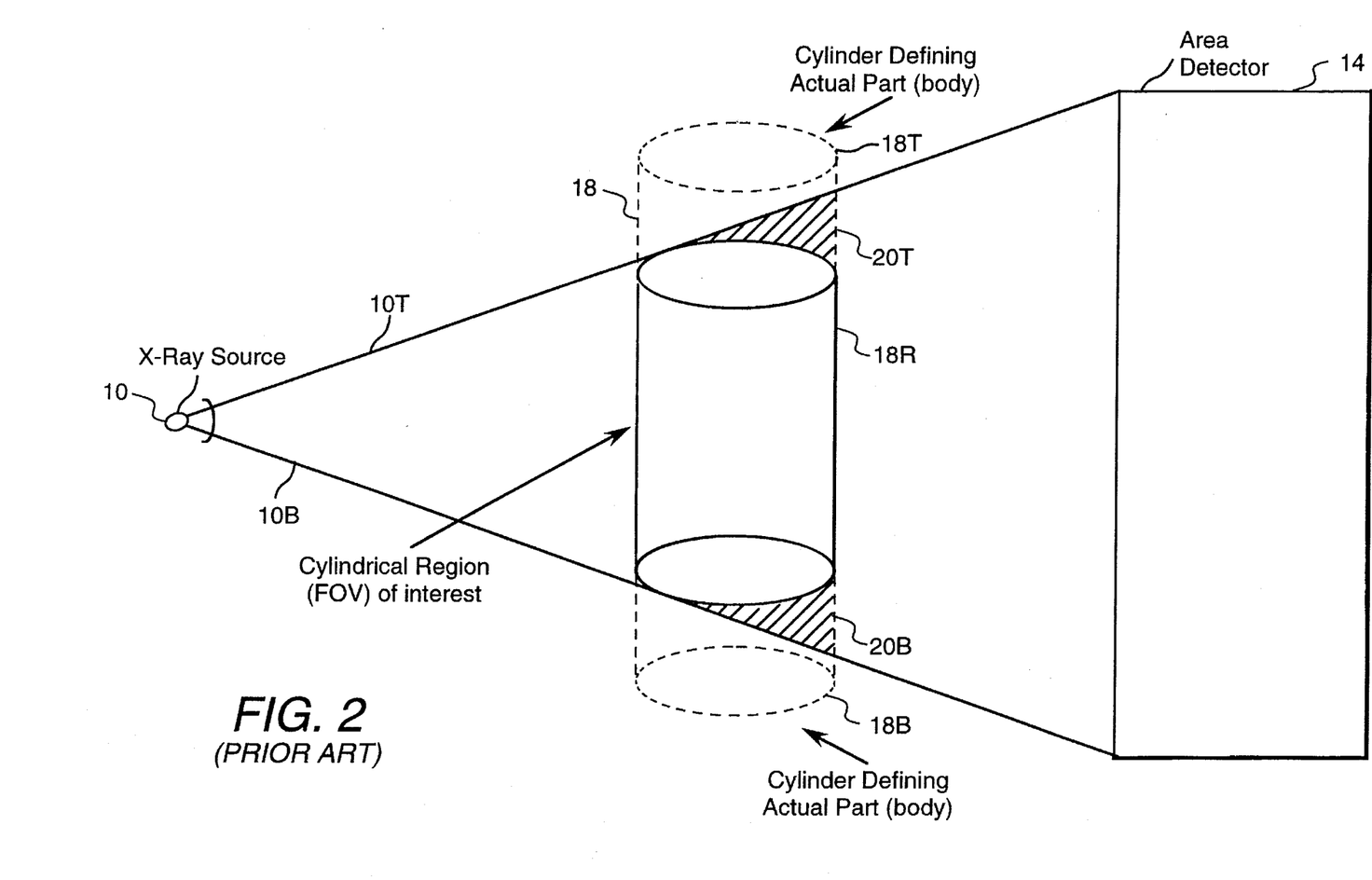
FIG. 2 illustrates a prior art problem where an object which is to be imaged is larger than the area detector can accommodate.

Turning now to prior art FIG. 2, a cylindrical object 18 includes a region of interest 18R within the field of view of x-ray source 10 and a top portion 18T and bottom portion 18B outside the region of interest 18R. For use of illustration, portions 18T and 18B are shown in phantom line.

Although the drawing of FIG. 2 does not show a scan path, a simply circular scan path similar to path 16 of FIG. 1 might be used. In that case, such a scan path would be an incomplete scan path (i.e., a scan path which provides incomplete data) for the same reasons as discussed with respect to FIG. 1. However, the FIG. 2 situation where the detector 14 is wide enough to span the part, but not high enough, causes a data corruption problem in addition to the incompleteness problem. Many ray paths between outer ray paths 10T and 10B pass through the part of the region of interest 18R and portions 20T and 20B, which are respectively portions of the portions 18T and 18B. For ease of illustration, the portions 20T and 20B have been shown with inclined lines. As a result of the ray paths passing through region of interest 18R and portions 20T and 20B, an image of the region of interest 18R cannot be unambiguously reconstructed from the data set collected. Effectively, the data relative to region of interest 18R is corrupted by portions 20T and 20B.

Figure 3:
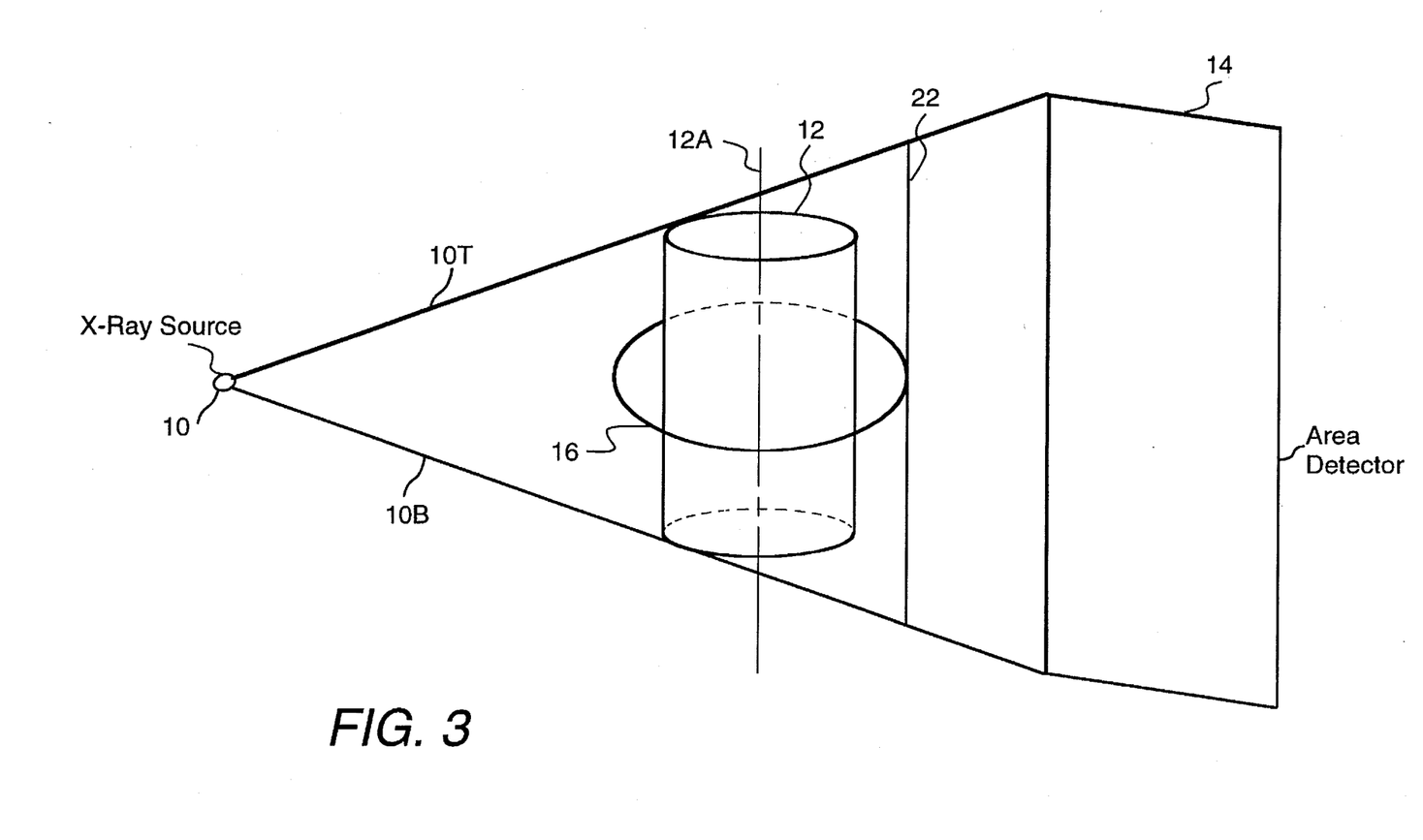
FIG. 3 illustrates schematically a circle and line scanning path according to the present invention.

With reference now to FIG. 3, the technique of the present invention for supplementing the data from the scan path 16 of FIG. 1 is illustrated schematically. FIG. 3 shows the same arrangement as FIG. 1 except that the original incomplete scan path 16 has been supplemented with a straight line scan 22 parallel to the cylinder central axis 12A and of sufficient length to assure that the completeness criterion is satisfied. In other words, the scan vertical line 22 would be sufficiently long that any plane that passing through the object 12 will intersect the scanning path corresponding to circle 16 and straight line 22 at least once. Note that 16 and 22 have been illustrated adjacent the object 12 for ease of illustration. This is simply to demonstrate the characteristics of the scan path. In practice, the circle corresponding to scan path 16 would be a circle centered at axis 12A and having a radius corresponding to the perpendicular distance between source 10 and axis 12A. Likewise, the vertical line of 22 would be disposed to pass through that circle.

FIG. 3 is useful for explaining a general principle of the present invention. Initially, an incomplete scan over a reasonable scan path is performed such as the circular scan corresponding to circle 16. If, following the incomplete scan path such as 16, more accurate information is required, the incomplete, initial data set (based on the sensed values from the detectors within area detector 14 during the scan of source 10 in a path corresponding to 16) will be supplemented. It is not necessary to repeat the scan corresponding to the circle 16. Instead, the data previously gathered from that scan may be combined with a supplemental data set obtained by a scan corresponding to line 22. The scan corresponding to line 22 may be accomplished by translating the cylindrical object 12 along a direction parallel to its central axis 12A. Alternately, the scan corresponding to line 22 may be accomplished by simultaneously moving source 10 and detector 14 (fixed relative to each other) in a vertical direction (i.e., parallel to central axis 12A).

By combining the initial data set from the circle scan 16 with the supplemental data set from the line scan 22 in known fashion, a combined data set is obtained. In this particular example, the combined data set will be a complete data set, meaning that the complete data acquisition criterion is satisfied.

Figure 4:
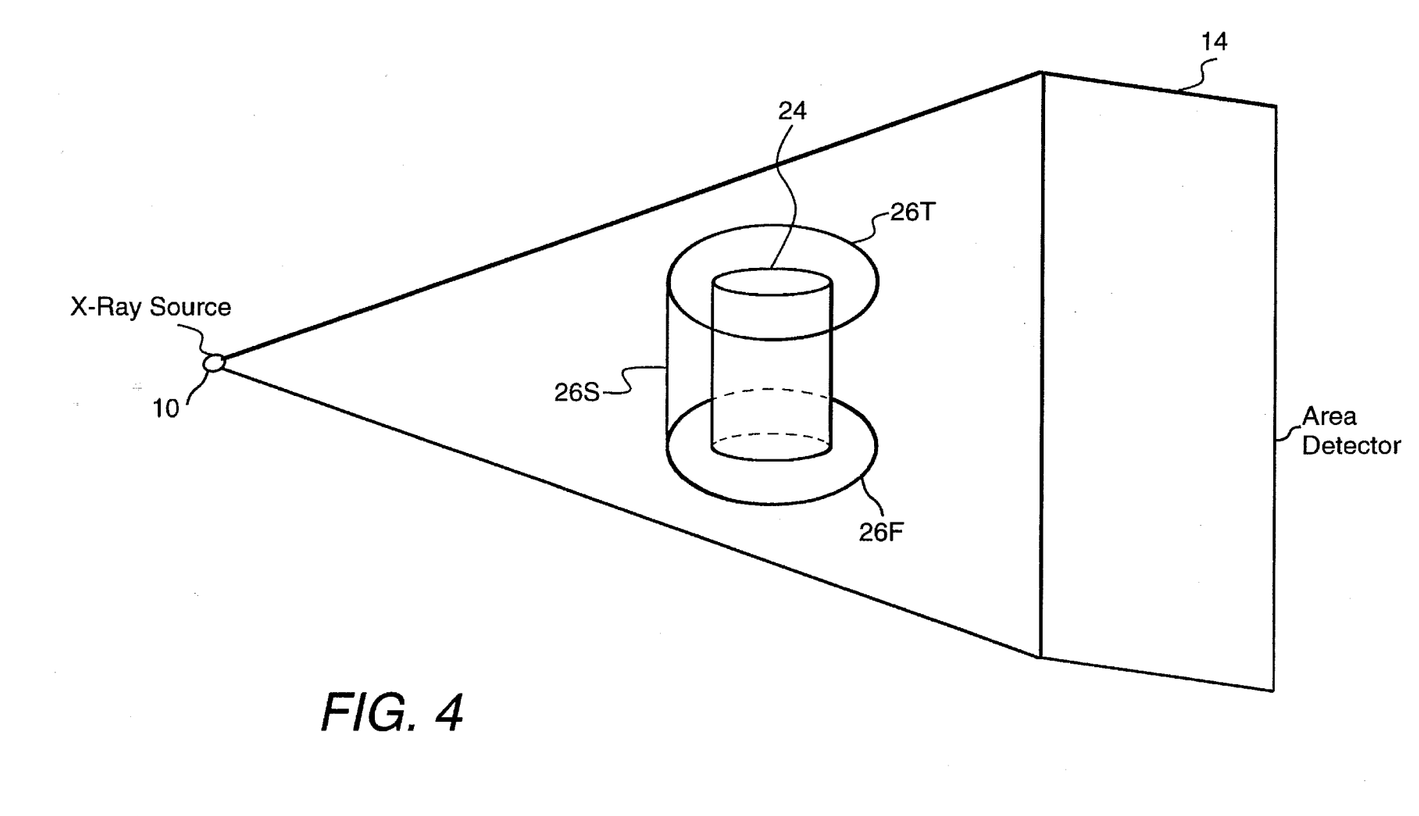
FIG. 4 illustrates a dual circle and line scan path according to the present invention.

Turning now to FIG. 4, a further example of the data acquisition technique of the present invention will be discussed. In FIG. 4, an object 24 is imaged by use of the source 10 and area detector 14. Initially, a first scan path 26F is used. The path 26F is a circle. As with the scan path illustrations of FIG. 3 and the figures discussed below, the scan path 26F and other portions of the scan path in FIG. 4 are illustrated adjacent the cylindrical object 24, but this is simply a convention for illustrative purposes. It will be understood that the circle 26F simply represents a scan path of the source 10 about a circle centered at the center of cylinder 24 and having a radius equal to the distance from source 10 to the central axis of cylinder 24.

After performing the scan 26F, an incomplete data set is acquired. If the incomplete data set is sufficient, no further data is necessary. However, if more accurate information is required, the initial, incomplete data set from the scan 26F may be supplemented by a scan path including a straight line second portion 26S and a circular third portion at 26T. This supplemental scanning corresponding to scan path portions 26S and 26T will provide a supplemental data set which may be combined in known fashion with the initial data set to provide a combined data set. Not only will this provide more accurate information, but it will satisfy the completeness criterion. In other words, the resulting combined data set will be complete in the manner discussed with respect to the Smith article previously incorporated by reference.

In the examples of FIGS. 3 and 4, an initial incomplete data set was completed by performing further scanning. However, it is sometimes not possible or not convenient to perform further scanning. An alternative to obtaining the supplemental data set by further scanning will be discussed with reference to FIG. 5.

Figure 5:
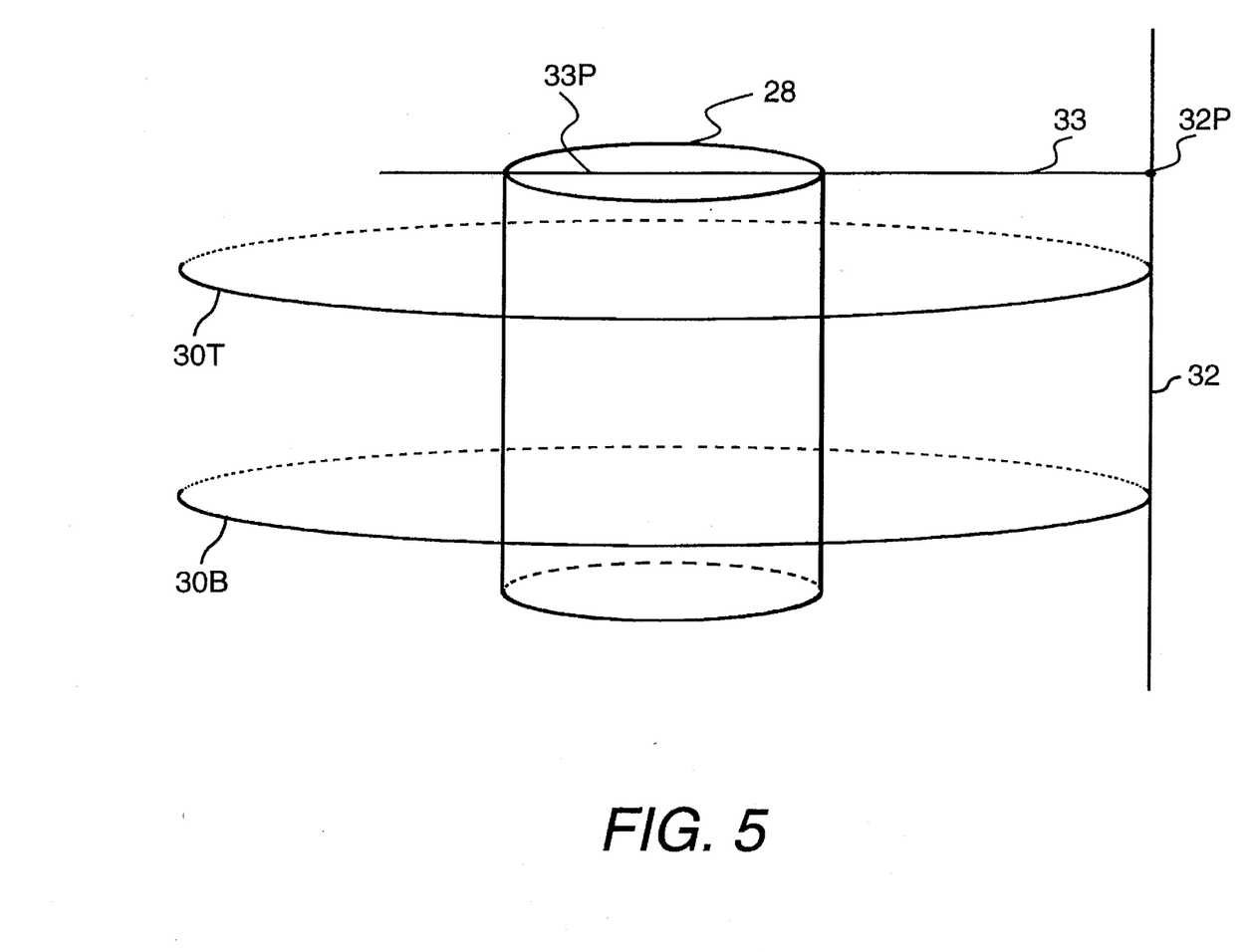
FIG. 5 illustrates a dual parallel circle scan path with simulated vertical scan line according to the present invention.

FIG. 5 is simplified such that a source and an area detector are not shown around the object 28 which is to be imaged. However, the top and bottom circles 30T and 30B together constitute an incomplete data scan path which would correspond to scanning of a source as discussed with respect to the previous figures. FIG. 5 additionally illustrates a vertical line simulated scan path 32.

Scanning the cylindrical object 28 by an incomplete scan path formed by the combination of circles 30T and 30B may well be satisfactory under many circumstances. For example, the object 28 might be a workpiece and the initial imaging using circles 30T and 30B is sufficient to show that it is reasonably defect-free. The object 28 might then be shipped to another location for assembly purposes. If one then decided that the object 28, or a portion of it, must have higher quality control than originally thought, it may be difficult or inconvenient to get the object 28 back for further scanning. Instead of performing further scanning, this technique would use data from the top circle 30T to reconstruct an approximate image of the part of the field of view above a plane centered in the end faces of cylindrical object 28 and parallel to the end faces. Data from the bottom circle 30B is used to reconstruct an approximate image of the part of the field of view below the previously mentioned plane. These approximate images (i.e., data corresponding to them) can then be used to calculate missing data required to provide a complete 3-D CT image under the criterion previously discussed. In the example, the approximate images corresponding to the top circle scan 30T and bottom circle scan 30D are used to calculate a simulated scan line 32 which, together with the actual and previously performed scan circle paths 30T and 30B satisfies the completeness criterion.

Data corresponding to the simulated scan line may be calculated based upon the approximate image information. For example, when the source (not shown in FIG. 5) is at point 32P, detector element (not shown) opposite to point 32P will receive ray 33 as attenuated by that portion 33P of ray 33 which passes through the top of 28. The signal which the detector element would receive can be calculated by summing with appropriate weighting factors the pixel values (from the approximate image) through which 33P passes. In similar fashion, the x-ray signals which other detector elements would detect when the source is at 32P can be calculated and this would be done at numerous points along line 32 to generate simulated scan data.

Figure 6:
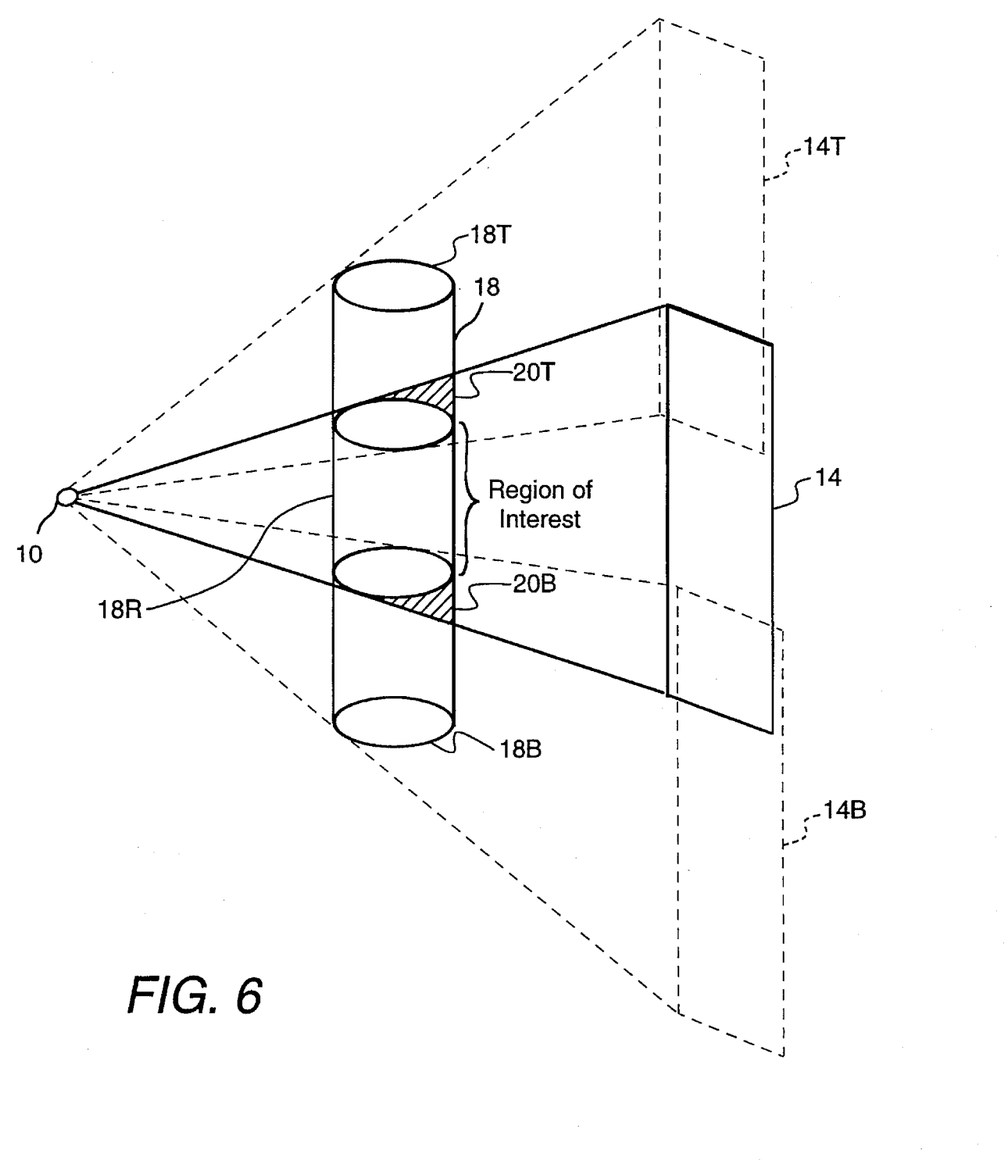
FIG. 6 shows a synthetic detector technique according to the present invention.

FIGS. 3–5 have addressed the general situation of prior art FIG. 1 where the data is incomplete. Turning to FIG. 6, a technique for handling the situation of FIG. 2, where the detector is not high enough to span the part, will be discussed. As indicated above in the discussion relative to FIG. 2, data relative to the region of interest 18R is corrupted by rays passing through portions 20T and 20B. In order to remove the corruption from the initial data set corresponding to region of interest 18R, the detector 14 may be moved from its solid line position to a phantom line position 14T and moved to a lower or bottom position 14B. Scanning would take place (scan path not shown) with source 10 and detector 14 in the relative positions indicated by the solid line corresponding to area detector 14. The area detector 14 could then be moved (relative to source 10) to the position corresponding to 14T. Scanning may then take place with source 10 and area detector 14 in those relative positions in order to provide image data relative to the upper portions of object 18 including top portion 18T. After scanning in those relative positions, the area detector 14 would be moved relative to the source 10 so that it assumes position 14B and scanning occurs in order to generate data corresponding to the lower portion of object 18 including bottom portion 18B. Note that it may be advantageous to move the detector 14 between its top position 14T and its bottom position 14B while keeping the source 10 stationary, then move the source 10 to a next position in its scan, then move detector 14 between its positions 14T and 14B, etc. In other words, instead of scanning source 10 completely for a given position of area detector 14 before moving the area detector 14, one could alternately move the area detector 14 to its various positions before moving source 10.

The approach of FIG. 6 simulates a larger area detector and is described in more detail in U.S. Pat. No. 5,319,693 issued on Jun. 7, 1994 in the name of the present inventors together with Kwok C. Tam, assigned to the assignee of the present application, and hereby incorporated by reference.

Figure 7:
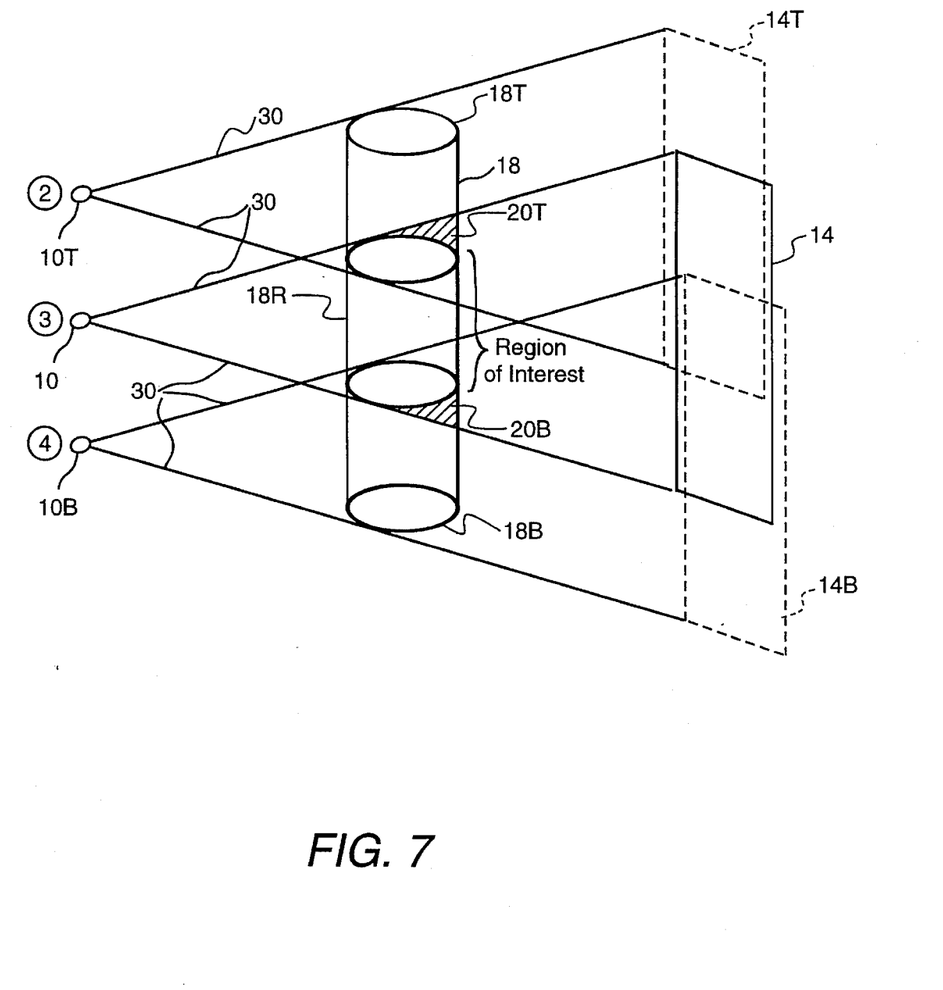
FIG. 7 shows an approximate sub-image synthetic detector method according to the present invention.

Turning now to FIG. 7, an alternative to the technique of FIG. 6 is shown where the source 10 moves between its initial middle position to a top position 10T when the detector 14 is moved to its top position 14T and the source moves to a bottom position 14B when the area detector 14 moves to its bottom position 14B. Scans (scan paths not shown) would be conducted with source 10 and area detector 14 in their top, middle, and bottom positions. Approximate images of each of the subsections intersected by the various rays passing between each pair of rays 30 would then be reconstructed. Recall that, with the source 10 and area detector 14 in their middle positions data relative region of interest 18R is corrupted by contributions from portions 20T and 20B. However, the approximate images reconstructed from the scans corresponding to source positions 10T and 10B can be used to calculate the contribution of both the region of interest and the portions 20T and 20B. Accordingly, an initial data set corresponding to region 18R can be combined with supplemental data to appropriately correct the projections along the edges of the region of interest 18R. This approach provides greatly enhanced images of the region of interest 18R. Since the goal is to accurately image region of interest 18R, this approach also allows one to scan or reconstruct images of portions 18T and 18B with lower resolution than used for region of interest 18R, thus allowing one to speed data acquisition, image reconstruction, and projection contributions. As is the case of the previously discussed techniques, this technique of FIG. 8 may be combined with use of a priori information in order to calculate missing projection data.

Figure 8:
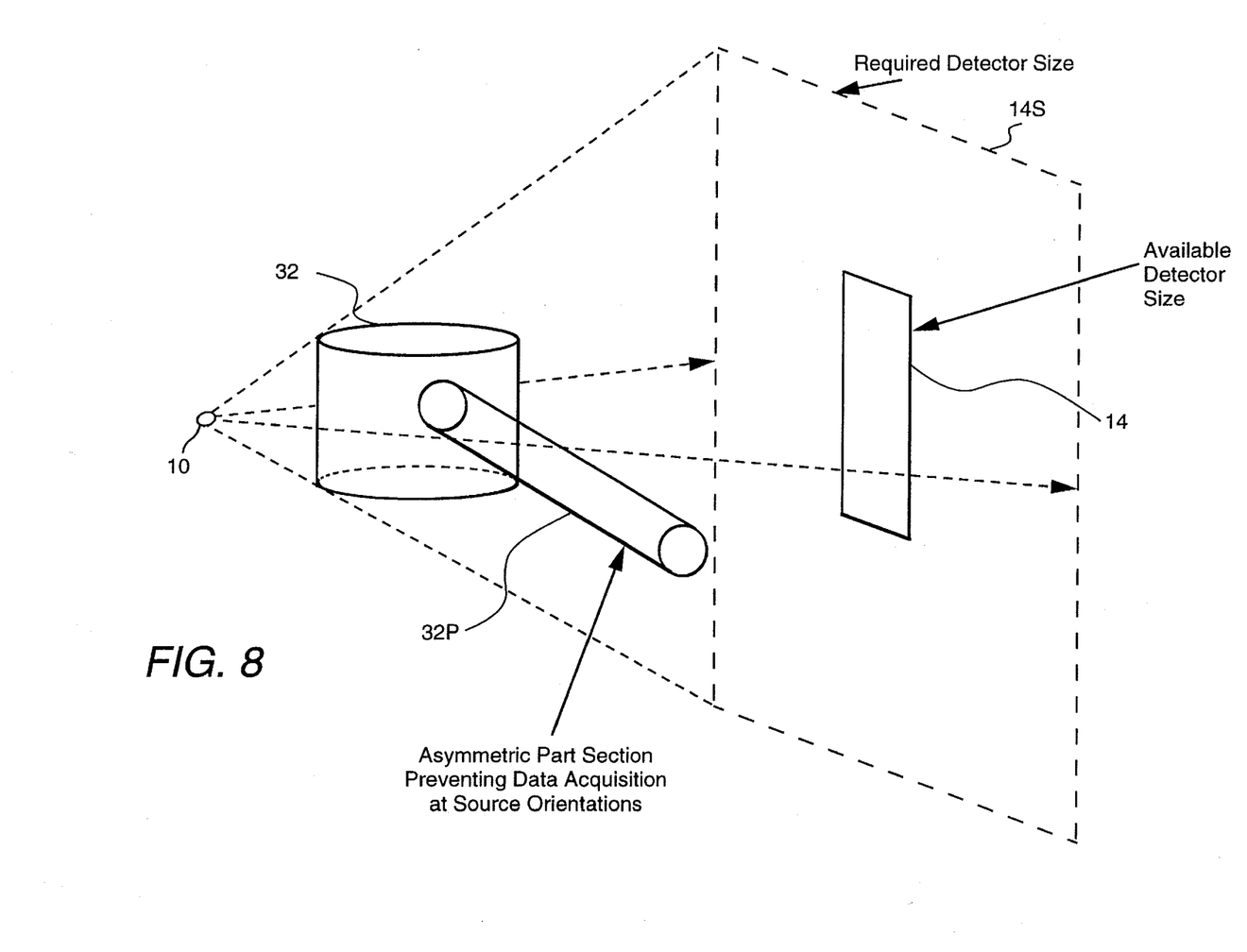
FIG. 8 shows how an irregular object may be imaged with the present invention.

Although the examples have used cylinders as the object which is to be imaged, it is to be appreciated that the objects for imaging may be irregular shapes. FIG. 8 shows an object 32 which is to be imaged by use of a source 10 and area detector 14. The object 32 is highly irregular and includes a portion 32P which prevents data acquisition at particular source orientations. Additionally, the object 32 is too large for the area detector 14. Accordingly, the area detector 14 may be scanned or moved to different locations using the technique described with respect to FIGS. 6 and 7 in order to relative a simulated detector size 14S. However, even for a particular location of detector 14, it may not be possible to scan completely. If the source 10 and detector 14 are scanned in incomplete patterns for a particular detector location, the approximate image approach discussed above, such as in connection with FIG. 5, may be used. Further, one could synthesize a simulated or synthetic area detector for completing projection data set in one direction and can use the approximate image technique for completing the data set in the other direction. For example, the detector could be repositioned from side-to-side over several scans to complete the projection data set in the horizontal direction, while the vertical part dimension could be covered by using approximate imaging of an adjacent region. Further, if the portion 32P is too large to fit between the source and detector at some orientations, a priori information can be used to determine missing projections for those orientations.

Several features of the present invention should be mentioned. With reference to the adjacent region approach discussed with reference to FIG. 7, the information about the adjacent regions can come from a design module of the object (a priori information), images of the adjacent region of the object which ignore end effects, images of the adjacent region of the object which use a simple model (e.g., uniform cylinder model) to determine end defects, additional data acquisition and imaging at one end of the object combined with positioning of the object so that the other end is within the detector aperture, or additional data acquisition and imaging at both ends of the object as previously described. Further, an iterative process may be required to achieve suitable image quality. In other words, one would construct and image the region of interest, use the information from the adjacent regions to enhance image quality, then use the region of interest image to enhance the images of the adjacent regions for use in the next step of region of interest enhancement. A further point which should be emphasized is that careful registration of the adjacent image sections is required. Additionally, a coarse scan or image in the adjacent subregions can be used to minimize the data acquisition and reconstruction load. Finally, calculation of the contribution of end effects to region of interest projections may take place using either image or projection data in the adjacent regions.

Figure 9:
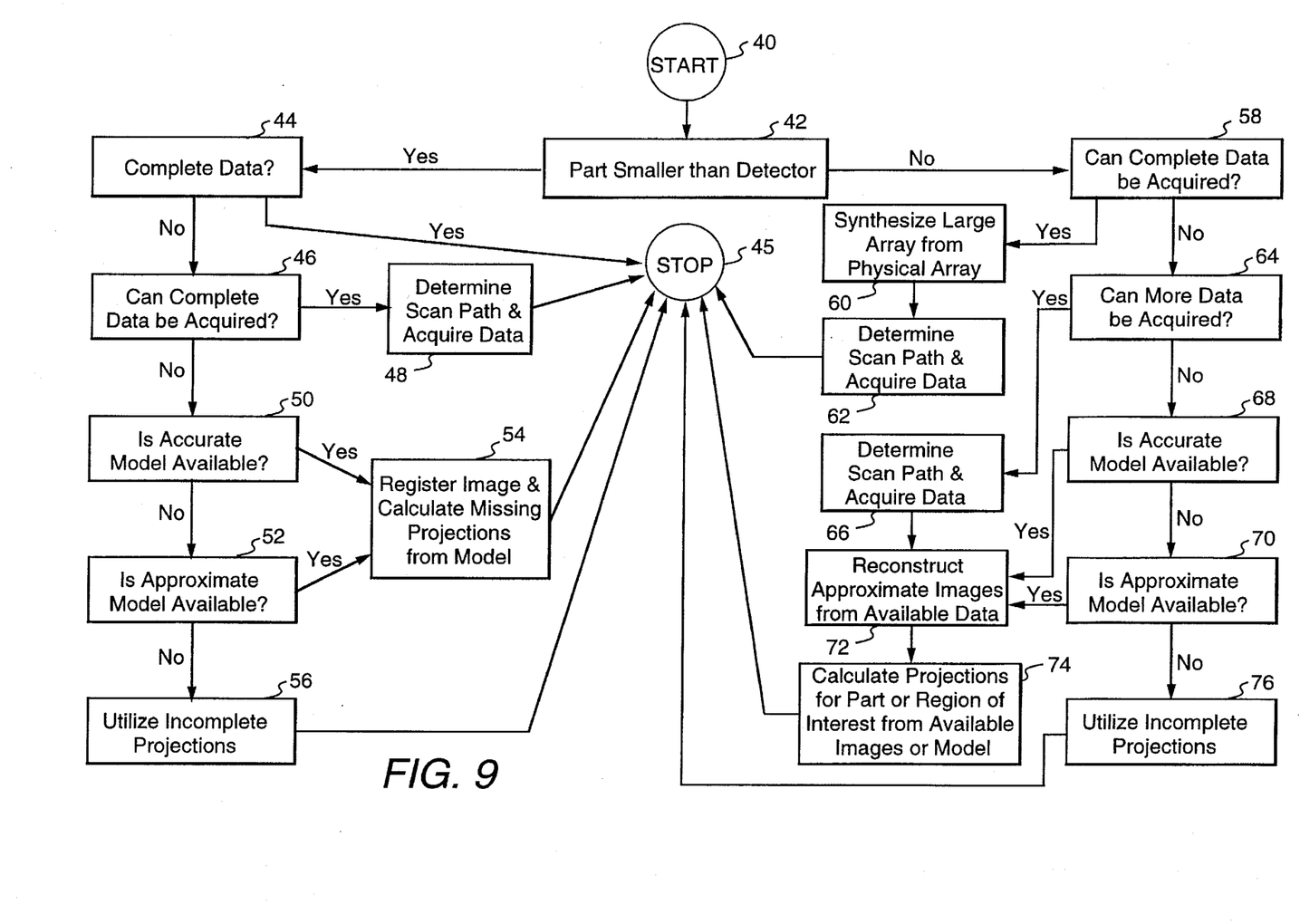
FIG. 9 is a flow chart illustrating the overall operation of the present invention.

With reference now to FIG. 9, the overall data aquisition approach of the present invention is illustrated by the flow chart. Proceeding from start block 40, block 42 tests to determine if the part is smaller than the detector. If so, block 42 goes to block 44 which tests to determine if the data is complete. If so, this leads to stop 45. However, if the data is not complete, block 44 leads to block 46 which tests to determine if complete data can be acquired. If so, block 48 determines the scan path and acquires the data corresponding to the supplemental data set.

If complete data cannot acquired, block 50 tests to determine if an accurate model is available. If not, block 52 tests to determine if an approximate model is available. If either of the models is available, block 54 will register the image and calculate the missing projections from the model. In other words, block 54 will calculate missing data by knowledge of the geometry of the object, its attenuation characteristics and the energy of the source. The missing projection data calculated from block 54 may be used to complete the data set from the initial incomplete scan.

If block 52 indicates that no approximate model is available, block 56 then utilizes incomplete projections for the images before returning to stop 45.

If block 42 indicates that the part is too large for the detector, block 58 tests to determine if complete data can be acquired. If so, block 60 may synthesize a large simulated detector array from the actual area detector. Block 62 then determines the scan path and acquires the data before going to stop 45. If complete data cannot be acquired after the test of block 58, block 64 tests to determine if more data may be acquired. If so, block 66 determines the scan path and acquires further data. If block 64 indicated that further data cannot be acquired, block 68 and 70 test to determine if an accurate or approximate model is available. If either model is available or if block 64 had lead to block 66, block 72 will then reconstruct the approximate images from the available data and lead to block 74 which calculates the projections for the region or part of interest from the available images or model.

If block 70 indicated that an approximate model was not available, block 76 then used incomplete projections before transferring to stop 45.

Figure 10:
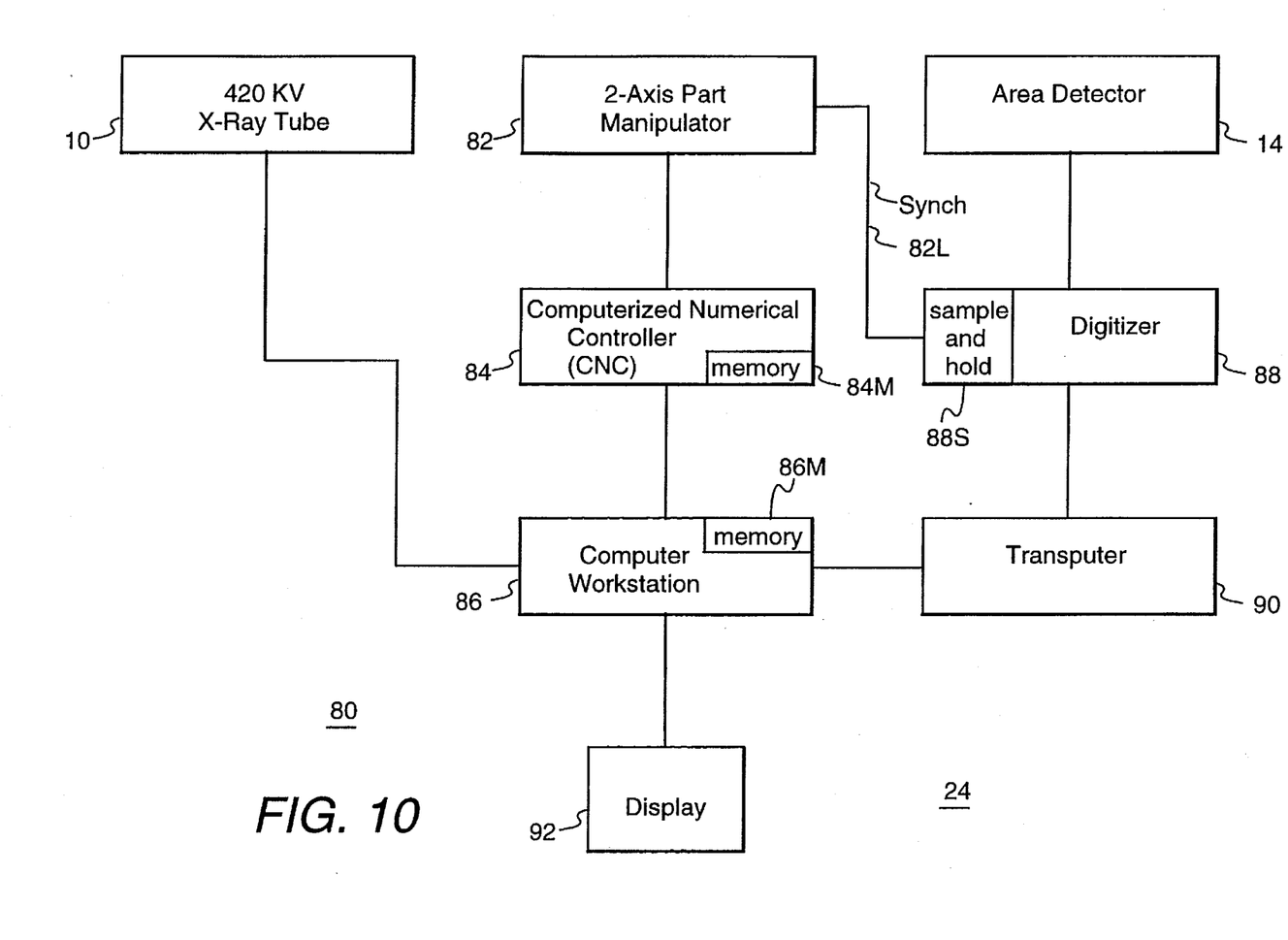
FIG. 10 is a simplified block diagram illustrating the system of the present invention.

Turning now to FIG. 10, a system 80 according to the present invention will be discussed including the source 10 and area detector 14. Although the source 10 has been shown as an x-ray tube, the cone beam source 10 could alternately provide neutrons, positrons, or other forms of radiation or electron magnetic energy from a point source. Alternately, other forms of imaging energy might be used.

A manipulator 82, which may be a two-axis part manipulator, is used to provide the relative scanning movement between the object (not shown in FIG. 10) which is used to be imaged and the source 10. Although the manipulator 82 is designed to move the object, the manipulator 82 might alternately move the source 10.

The manipulator 82 is controlled by a known computerized numerical controller 84, which may, for example, be of a type made by Aerotech. The controller 84 may include a memory 84M having data defining various scan paths in known fashion. Alternately, also using well known techniques, a memory 86M of a computer work station 86, which is connected to the controller 84, may have the data which defines movements of the manipulator 82 and therefore defines the scan path or trajectory. The computer work station 86 may be a work station made by Sun, although other computer work stations and possibly even personal computers might be used in place of the work station. The computer work station controls the other components of the system 80 in known fashion.

Connected to the area detector 14 is a digitizer 88 which operates in known fashion to convert analog signals from the area detector into digital signals representative of the image of the object under test. The digitizer 88 may include sample and hold circuits 88S operating in response to a synch signal on line 82L in known fashion.

The digitized values corresponding to the sense radiation from the detector elements within detector 14 are supplied the digitizer 88 to a transputer 90. The transputer 90, which may be of a known commercially available type such as a Meiko M40, is an array processor which provides the necessary signal processing for the signals coming from the digitizer 88. The transputer 90 may perform the necessary image processing such that a display might be connected directly to the transputer to display the images from the CT scan. However, in the arrangement shown in FIG. 10, the process data from transputer 90 is supplied to computer work station 86 and the computer work station 86 in turn supplies the data, with or without further processing, to a display 92 which displays the CT images.

The memory 85M includes a portion serving as a means for receiving an initial data set corresponding to an incomplete scan path. Additionally, the memory 86M contains a means for causing the acquisition of a supplemental data set representative of image information about the region of interest. For example, and referring back momentarily to FIG. 3, if the initial data set corresponds to the circular scan 16, an operator may look at the display 92 and decide that the particular object 12 requires more accurate imaging information. The operator would then instruct the computer work station 86 to execute a program within memory 86M to cause manipulator 82 to scan along the supplemental scan path 22 of FIG. 3. This will result in the memory 86M receiving a supplemental data set representative of image information about the object 12. The program within memory 86M may then use known techniques for combining the supplemental data set with the initial data set to provide a combined data set.

The FIG. 9 technique would be stored as a program in memories 84M and/or 86M and would have the ability to store data of a 3D model of the object so as to provide a priori information and/or to help calculate ray path intersections with the object as discussed.

Although various specific constructions have been given for the present invention, it is to be understood that these are for illustrative purposes only. Various modifications and adaptations will be readily apparent to those of skill in the art. For example, although the present invention has been described with reference to a source which physically moves relative to the object during the scanning operation, an alternative is possible. In such an alternative, a material may be around or partially around the object to be viewed, which material generates imaging energy upon being struck by a different kind of energy beam. The beam applied to the source material causes the source material to in turn emit an imaging energy. Although the source is not physically moved relative to the object, the source would effectively be moved relative to the object by sweeping the beam striking the source material in a path corresponding to the trajectory. In similar fashion and as used herein, moving the source relative to the object shall include situations where a series of sources are turned on sequentially to effectively move the source as well as the beam striking a source material type of source movement. In view of these and other modifications, the scope of the present invention should be determined by reference to the claims appended hereto.

What is claimed is:

1. A method of three-dimensional computerized tomography imaging of at least a region of interest of an object subject to imaging energy, the method comprising the steps of:

applying imaging energy from a source to the object;

moving the source relative to the object in a first scan path covering a full circle, the first scan path generating an incomplete initial data set wherein some planes passing through the object are able to intersect a projection of the imaging energy from the source along the first scan path in at least one location and some planes passing through the object are unable to intersect a projection of the imaging energy from the source along the first scan path in at least one location;

acquiring the incomplete, initial data set relative to the region of interest from the first scan path by using an area detector to sense the imaging energy;

obtaining a supplemental data set of image information that is at least partially representative of the region of interest, said obtaining step is performed by using a first portion of data from a first portion of said incomplete initial data set corresponding to an approximate image of a first part of said region of interest, using a second portion of data from a second portion of said incomplete initial data set corresponding to an approximate image of a second part of said region of interest, and using the first and second portions of data to determine said supplemental data set, said obtaining step further performed by acquiring first adjacent data corresponding to an approximate image of a first adjacent region adjacent to said region of interest and acquiring second adjacent data corresponding to an approximate image of a second adjacent region adjacent to said region of interest;

combining the supplemental data set with the incomplete initial data set to provide a complete combined data set wherein every plane passing through the object is able to intersect a projection of the imaging energy from the source along the first scan path in at least one location, said combining step correcting projections at the edges of the region of interest to remove portions from the first and second adjacent regions; and displaying an image of at least the region of interest of the object based upon said combined data set.

2. The method of claim 1 wherein the obtaining step is performed by using a priori information about the object to provide missing projection data.

3. The method of claim 1 wherein said supplemental data set contains data corresponding to a second scan path that simulates a scan path separate and apart from the first scan path, which, combined with said first scan path, constitutes a third scan path, wherein every plane passing through the object is able to intersect a projection of the imaging energy from the source along the first and second scan paths in at least one location.

4. A three-dimensional computerized tomography system comprising:

a source of imaging energy for applying imaging energy to at least a region of interest of an object;

a two-dimensional area detector positioned to receive imaging energy from said source;

scanning means for causing relative motion of said source and the object such that said source moves along a first scan path relative to the object covering a full circle, the first scan path generating an incomplete initial data set wherein some planes passing through the object are able to intersect a projection of the imaging energy from the source along the first scan path in at least one location and some planes passing through the object are unable to intersect a projection of the imaging energy from the source along the first scan path in at least one location, said area detector sensing imaging energy generated from the first scan path to provide the incomplete initial data set;

means for receiving said incomplete initial data set from said area detector;

means for obtaining a supplemental data set that is at least partially representative of image information about the region of interest, said obtaining means using a first portion of data from a first portion of said incomplete initial data set corresponding to an approximate image of a first part of said region of interest, using a second portion of data from a second portion of said incomplete initial data set corresponding to an approximate image of a second part of said region of interest, and using the first and second portions of data to determine said supplemental data set, said obtaining means acquiring first adjacent data corresponding to an approximate image of a first adjacent region adjacent to said region of interest and acquiring second adjacent data corresponding to an approximate image of a second adjacent region adjacent to said region of interest;

means for combining the supplemental data set with the incomplete initial data set to provide a complete combined data set wherein every plane passing through the object is able to intersect a projection of the imaging energy from the source along the first scan path in at least one location, said combining means correcting projections at the edges of the region of interest to remove portions from the first and second adjacent regions;

a display, operably connected to said combining means for displaying an image of the region of interest based upon the combined data set.

5. The system of claim 4 wherein said obtaining means causes said scanning means to scan in a second scan path, wherein the second scan path obtains additional data supplementing the incomplete initial data set generated from the first scan path which, combined with the first scan path constitutes a third scan path, wherein every plane passing through the object is able to intersect a projection of the imaging energy from the source along the first and second scan paths in at least one location.

6. The system of claim 4 wherein said supplemental data set is generated by using a priori information about the object.

* * * * *